(12) United States Patent
Estrada et al.

(10) Patent No.: US 8,880,363 B2
(45) Date of Patent: *Nov. 4, 2014

(54) METHOD AND APPARATUS FOR THE MEASUREMENT OF THE MASS FRACTION OF WATER IN OIL-WATER MIXTURES

(75) Inventors: Herbert Estrada, Annapolis, MD (US); Calvin R. Hastings, Mt. Lebanon, PA (US); Donald R. Augenstein, Pittsburgh, PA (US)

(73) Assignee: Cameron International Corporation, Houston, TX (US)

( * ) Notice: Subject to any disclaimer, the term of this patent is extended or adjusted under 35 U.S.C. 154(b) by 659 days.

This patent is subject to a terminal disclaimer.

(21) Appl. No.: 13/066,354

(22) Filed: Apr. 13, 2011

(65) Prior Publication Data

US 2011/0246099 A1 Oct. 6, 2011

Related U.S. Application Data

(63) Continuation-in-part of application No. 12/383,431, filed on Mar. 24, 2009, now Pat. No. 8,532,943.

(51) Int. Cl.
*G01N 29/024* (2006.01)
*G01N 33/28* (2006.01)

(52) U.S. Cl.
CPC .... *G01N 33/2847* (2013.01); *G01N 2291/0224* (2013.01); *G01N 29/024* (2013.01); *G01N 2291/0222* (2013.01)
USPC .......................................... 702/48; 73/861.29

(58) Field of Classification Search
CPC .......................... G01N 33/2847; G01N 29/024
USPC ...................... 702/48, 127; 73/861.28, 861.29
See application file for complete search history.

(56) References Cited

U.S. PATENT DOCUMENTS

| 3,409,048 A | 11/1968 | Brown |
| 3,892,127 A | 7/1975 | Cirulis et al. |
| 4,059,987 A * | 11/1977 | Dowling et al. ............. 73/61.43 |
| 4,080,837 A | 3/1978 | Alexander et al. |

(Continued)

OTHER PUBLICATIONS

Xu, "Study on oil-water two-phase flow in horizontal pipelines", 2007, Elsevier, J. Petro. Sci. & Eng., 59, pp. 43-58.*
Yuguang Liu, "Acoustic Properties of Reservoir Fluids", Jun. 1998, PhD Dissertation Stanford University, Chapter 5, pp. 69-88.*

(Continued)

*Primary Examiner* — Jonathan C Teixeira Moffat
*Assistant Examiner* — Regis Betsch
(74) *Attorney, Agent, or Firm* — Ansel M. Schwartz

(57) ABSTRACT

An apparatus for measuring the mass fractions of water and oil in a flowing mixture of oil and water through a pipe includes a sensor portion that measures sound velocity and temperature of the flowing oil water mixture at a first time and at a second time. The apparatus includes a temperature changer in thermal communication with the flowing fluid which changes the temperature of the flowing oil water mixture by a measurable amount between the first time and the second time. A method for measuring water mass fraction in a flowing mixture of oil and water through a pipe includes the steps of measuring sound velocity and temperature of the flowing oil water mixture at a first time with a sensor portion. There is the step of changing the temperature of the flowing oil water mixture by a measurable amount with a temperature changer in thermal communication with the flowing fluid. There is the step of measuring sound velocity and temperature of the flowing oil water mixture at a second time with the sensor portion.

21 Claims, 8 Drawing Sheets

(56) References Cited

U.S. PATENT DOCUMENTS

| | | | |
|---|---|---|---|
| 4,142,414 A * | 3/1979 | Cosentino | 73/216 |
| 4,150,561 A | 4/1979 | Zupanick | |
| 4,170,894 A | 10/1979 | Zupanick | |
| 4,236,406 A * | 12/1980 | Reed et al. | 73/61.45 |
| 4,442,720 A * | 4/1984 | Apley et al. | 73/863.31 |
| 4,656,869 A * | 4/1987 | Zacharias | 73/597 |
| 4,891,969 A * | 1/1990 | Wayland et al. | 73/61.44 |
| 4,938,066 A * | 7/1990 | Dorr | 73/597 |
| 5,285,675 A | 2/1994 | Colgate et al. | |

OTHER PUBLICATIONS

M. Fingas et al., "Chapter 18: Environmental Emulsions," Encyclopedic Handbook of Emulsion Technology, Mercel Dekker, Inc., (Mar. 2001).

A. Peña et al., "Chemically Induced Destabilization of Water-in-Crude Oil Emulsions," Ind. Eng. Chem. Res., 44, p. 1139-1149, (2005).

Xu, Xiao-Xuan, "Study on oil-water two-phase flow in horizontal pipelines," J. Petro. Sci. & Eng. 59(2007) 43-58, p. 47-48.

Day, Michael, "No-Slip Condition of Fluid Dynamics," Erkenntnis, vol. 33 (No. 3), p. 285-296, (1990).

\* cited by examiner

METHOD AND APPARATUS FOR THE MEASUREMENT OF THE MASS FRACTION OF WATER IN OIL-WATER MIXTURES

CROSS-REFERENCE TO RELATED APPLICATIONS

This is a continuation-in-part of U.S. patent application Ser. No. 12/383,431 filed Mar. 24, 2009 now U.S. Pat. No. 8,532,943.

FIELD OF THE INVENTION

The present invention is related to the measurement of the mass fractions of water and oil in a flowing mixture of oil and water through a pipe. (As used herein, references to the "present invention" or "invention" relate to exemplary embodiments and not necessarily to every embodiment encompassed by the appended claims.) More specifically, the present invention is related to the measurement of the mass fractions of water and oil in a flowing mixture where a temperature changer changes the temperature of the flowing oil water mixture by a measurable amount between a first time and a second time so the mass fraction can be determined from the change in the sound velocity in the mixture for a known change in temperature.

BACKGROUND OF THE INVENTION

This section is intended to introduce the reader to various aspects of the art that may be related to various aspects of the present invention. The following discussion is intended to provide information to facilitate a better understanding of the present invention. Accordingly, it should be understood that statements in the following discussion are to be read in this light, and not as admissions of prior art.

Recent years have seen increased need for an accurate measurement of the water cut—the fraction by volume of water in crude oil relative to the total volume of the mixture. The need has arisen because of the increased use of water and steam for the extraction of crude oil from depleted fields, and because of increased transport of crude by tankers to refineries remote from the field—the transporting tankers often maintain a nominally fixed ballast condition by introducing seawater into oil storage tanks.

Accurate measurement of water cut has proven difficult:
1. Several systems that endeavor to correlate the capacitance of the oil water mixtures with water cut are commercially available. These systems suffer however from several technical difficulties: (a) For high water cuts, the mixture's conductance becomes high and capacitance is a poor measure of the water content; and (b) The relationship between the inter-electrode capacitance (or resistance) may not characterize the true mass or volume fraction of water in the flowing fluid, because the distribution of the phases does not correlate with the electrostatic field intensity.
2. Experiments have shown that, under certain conditions, measurement of the sound velocity of an oil-water mixture can be used to characterize the mass fractions of water and oil in the mixture. There are however several drawbacks to this method: (a) An accurate measure of the sound velocity and specific gravity of each of the two phases is required and (b) The method becomes increasingly inaccurate as the sound velocity and specific gravity of one phase approaches that of the other (this situation can occur with heavy crudes).
3. Many rely on batch sampling of the flowing process fluid for the measurement of water cut, with the separation and weighing of the phases performed off-line. This method has several obvious drawbacks: (a) It is labor intensive, (b) The uncertainties as to how well the sample represents the whole are difficult to bound, and (c) The sample data are not available in real time to allow action in response to a sudden change in water cut.

The water cut measurement of the present invention draws on the technology of technique 2 above, but overcomes its difficulties, as well as those of the other techniques, by a unique and hitherto unexploited approach.

BRIEF SUMMARY OF THE INVENTION

The present invention pertains to the measurement of the mass fraction of water in oil-water mixtures. The measurement is performed using ultrasonic transducers. The measurement is based on the fact that the mass fraction is related to the change in the sound velocity in the mixture for a known change in temperature.

BRIEF DESCRIPTION OF THE SEVERAL VIEWS OF THE DRAWING

In the accompanying drawings, the preferred embodiment of the invention and preferred methods of practicing the invention are illustrated in which.

DETAILED DESCRIPTION OF THE INVENTION

Figure 9:
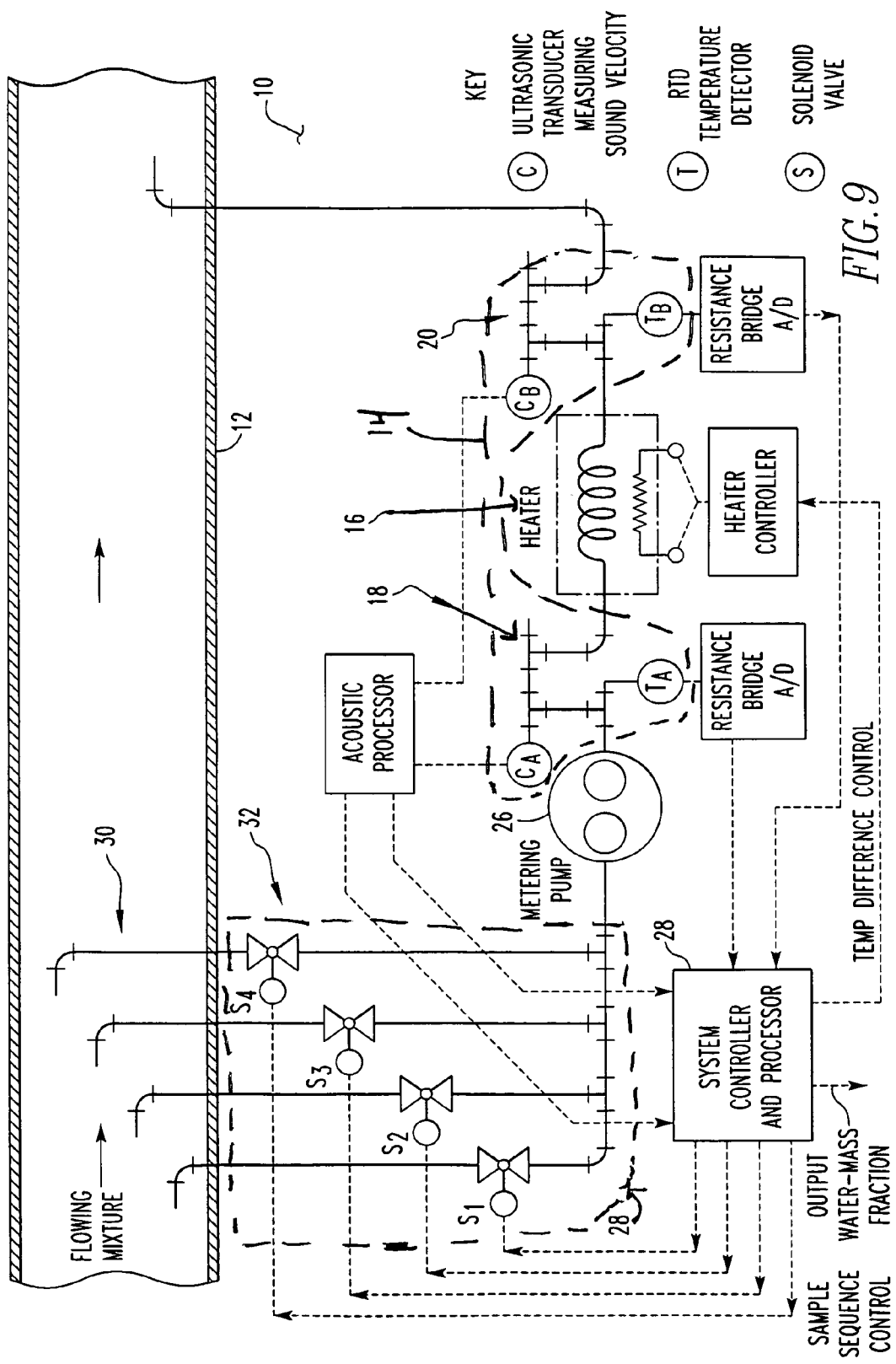
FIG. 9 is a flow diagram of measurement of the mass fraction of water, in water-oil mixtures of the present invention.
Figure 10:
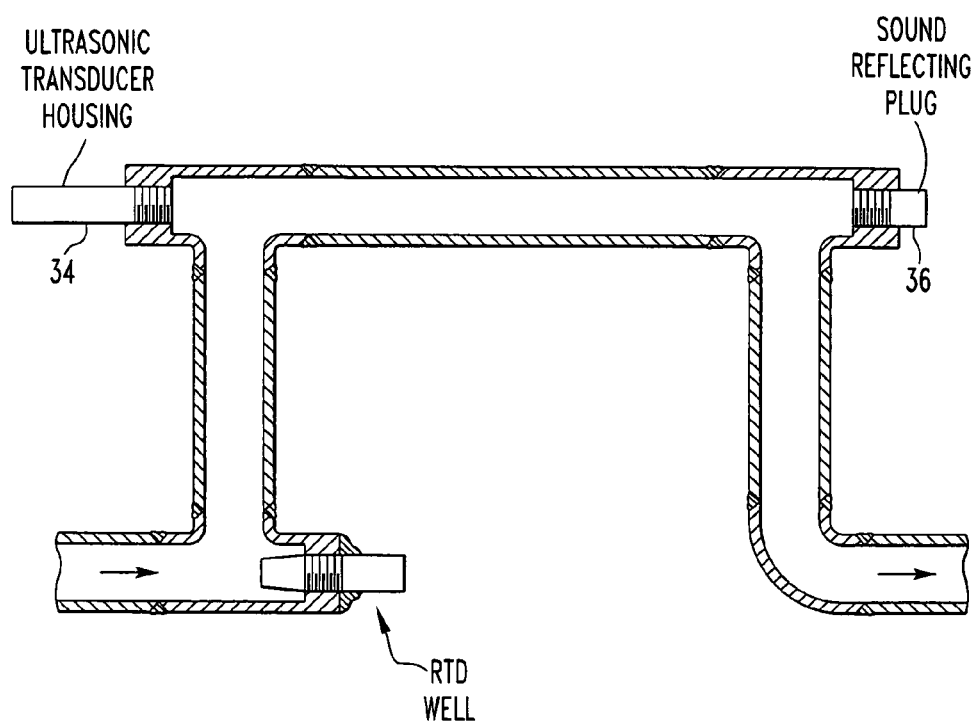
FIG. 10 shows temperature and sound velocity sensor assembly of the present invention.

Referring now to the drawings wherein like reference numerals refer to similar or identical parts throughout the several views, and more specifically to FIGS. 9 and 10 thereof, there is shown an apparatus 10 for measuring the mass fractions of water and oil in a flowing mixture of oil and water through a pipe 12. The apparatus 10 comprises a sensor portion 14 that measures sound velocity and temperature of the flowing oil water mixture at a first time and at a second time. The apparatus 10 comprises a temperature changer 16 in thermal communication with the flowing fluid which changes the temperature of the flowing oil water mixture by a measurable amount between the first time and the second time.

The sensor portion 14 can include a first sensor portion 18 that measures the sound velocity and temperature of the flowing oil water mixture upstream of the temperature changer 16, and a second sensor portion 20 that measures the sound velocity and temperature of the flowing mixture downstream of the temperature changer 16. The temperature changer 16 can be either a heat exchanger that adds thermal energy to, or a cooler that removes thermal energy from the flowing mixture.

The apparatus 10 can include a controller 22 and processor 24 that determine the mass fraction of the water and oil through an algorithm stored on a computer readable medium which is executed by the controller 22 and processor 24 that relates the mass fraction to the change in the sound velocity in the mixture for a known change in temperature. The oil water mixture can be emulsified so that droplets of a dispersed phase, which is either oil or water, are distributed throughout a continuous phase, which is either water or oil. The dispersal can be achieved by the flowing mixture moving at a velocity sufficient to achieve emulsification with essentially no slip. The apparatus 10 can include a pump 26 in fluid communication with the mixture to ensure the velocity of the sample mixture is made to meet or exceed the emulsification velocity requirement and wherein a portion of the flowing oil water mixture is continuously sampled and passed through the first and second sensor portions 18, 20 and the temperature changer 16 so as to allow determination of the change in mixture sound velocity for a measured change in temperature.

In another embodiment, the apparatus 10 can include a pump 26 in fluid communication with the mixture to ensure the velocity of the sample mixture is made to meet or exceed the emulsification velocity requirement and wherein several portions of the flowing oil water mixture are sampled, either continuously or successively. The samples, either singly or in combination, can pass through the first and second sensor portions 18, 20 and the temperature changer 16 so as to allow the determination of the change in mixture sound velocity for a measured change in temperature for each sample location.

The apparatus 10 can include a sampling arrangement 28 for sampling the fluid in communication with the first sensor portion 18. The sampling arrangement 28 can include a plurality of taps 30 disposed at different radii in the pipe 12 which sample the mixture. The sampling arrangement 28 can include valves 32 for each tap that are maintained open for a period long enough to ensure a representative sound velocity and temperature measurement for the associated tap location.

The first sensor portion 18 can include a sound velocity transducer 34 and a reflecting plug 36. The sound velocity C of the mixture can be determined from the transit time t of a pulse of ultrasound from the transducer that travels to the reflecting plug 36 of the sensor and back to the transducer.

The present invention pertains to a method for measuring a water mass fraction in a flowing mixture of oil and water through a pipe 12. The method comprises the steps of measuring sound velocity and temperature of the flowing oil water mixture at a first time with a sensor portion 14. There is the step of changing the temperature of the flowing oil water mixture by a measurable amount with a temperature changer 16 in thermal communication with the flowing fluid. There is the step of measuring sound velocity and temperature of the flowing oil water mixture at a second time with the sensor portion 14.

The measuring step at a first time can include the step of measuring the sound velocity and temperature of the flowing oil water mixture with a first sensor portion 18 of the sensor portion 14 upstream of the temperature changer 16, and the measuring step at a second time includes the step of measuring the sound velocity and temperature of the flowing oil water mixture with a second sensor portion 20 of the sensor portion 14 downstream of the temperature changer 16. The temperature changer 16 can be either a heat exchanger that adds thermal energy to, or a cooler that removes thermal energy from the flowing mixture.

There can be the step of determining the mass fraction of the water through an algorithm stored on a computer readable medium which is executed by a controller 22 and processor 24 that relates the mass fraction to the change in the sound velocity in the mixture for a known change in temperature.

There can be the step of emulsifying the oil water mixture so that droplets of a dispersed phase, which is either oil or water, are distributed throughout a continuous phase, which is either water or oil, said dispersal achieved by the flowing mixture moving at a velocity sufficient to achieve emulsification with essentially no slip. ["no slip" means the velocities of the two components of the mixture are equal.]

There can be the step of pumping the mixture with a pump 26 in fluid communication with the mixture to ensure the velocity of the sample mixture is made to meet or exceed the emulsification velocity requirement and wherein a portion of the flowing oil water mixture is continuously sampled and passed through the first and second sensor portions 18, 20 and the temperature changer 16 so as to allow determination of the change in mixture sound velocity for a measured change in temperature.

In an alternative embodiment, there can be the step of pumping the mixture with a pump 26 in fluid communication with the mixture to ensure the velocity of the sample mixture is made to meet or exceed the emulsification velocity requirement and wherein several portions of the flowing oil water mixture are sampled, either continuously or successively, said samples, either singly or in combination pass through the first and second sensor portions 18, 20 and the temperature changer 16 so as to allow the determination of the change in mixture sound velocity for a measured change in temperature for each sample location.

There can be the step of sampling the fluid with a sampling arrangement 28 in communication with the first sensor portion 18. The sampling step can include the step of sampling the mixture with a plurality of taps 30 disposed at different radii in the pipe 12 of the sampling arrangement 28.

There can be the step of maintaining open valves 32 of each tap of the sampling arrangement 28 for a period long enough to ensure a representative sound velocity and temperature measurement for the associated tap location. There can be the step of determining the sound velocity C of the mixture from the transit time t of a pulse of ultrasound from a transducer that travels to a reflecting plug 36 of the first sensor portion 18 and back to the transducer.

In the operation of the invention, sound velocity—the propagation velocity of a pressure wave through a physical medium—is a function of the ratio of the stiffness and the density of the medium. For a sound velocity measurement to characterize the components of an oil-water mixture, the two phases must be dispersed, so that the stiffness and density of each component of the mixture participate in the pressure wave propagation. Furthermore, the length of the pressure wave must be long compared to the dimensions of the dispersed phase, to prevent the multiple phase interfaces in the wave path from excessively scattering the acoustic energy.

When an oil-water mixture flows at a velocity in excess of 4 to 10 feet per second, the mixture starts to emulsify—one of the two phases becomes dispersed. Emulsification is often complete at velocities of 10 feet per second, though higher velocities may be necessary in some circumstances. If the oil fraction is high, the water disperses in the oil; if the water fraction is high, the opposite occurs. But in both cases the droplets of the dispersed phase are small and pulses of ultrasound, at frequencies up to 1 MHz or more can be transmitted and received through distances long enough to make various ultrasonic measurements practical.

A derivation of the relationship between the sound velocity of a mixture of oil and water and the sound velocities and other properties of its constituents follows.

In the absence of slip* the specific volume v of the mixture of oil and water is given by:

* The term slip is used to describe a state in which one phase of a two phase mixture is traveling at a different mass velocity than the other phase. The absence of slip means that the two mass velocities are equal $$v = Xv_1 + (1-X)v_2 \quad (1)$$

Here The subscripts 1 and 2 refer to water and oil respectively

X is the fraction of the mixture, by weight, that is water. More precisely, $X = W_1/(W_1+W_2)$, where the W's are mass flow rates.

The mixture density, ρ is the reciprocal of the specific volume:

$$\rho = 1/v \quad (2)$$

The densities of the mixture components are similarly related to their specific volumes.

The sound velocity c of the mixture is related to the mixture density by the following:

$$c^2 = g \partial P/\partial \rho|_s \quad (3)$$

Here g is the gravitational constant

P is pressure s is entropy

Similar relationships apply to the sound velocities of the mixture components.

Expressing equation 2 as a differential:

$$d\rho = -dv/v^2 \quad (4)$$

Using this relationship to express the reciprocal of the sound velocity in terms of pressure and specific volume:

$$1/c^2 = -(1/gv^2) \partial v/\partial P|_s \quad (5)$$

Or:

$$\partial v/\partial P|_s = -(gv^2)/c^2 \quad (6)$$

The partial derivative of equation (1) with respect to pressure at constant entropy yields the relationship between the sound velocity of the mixture and its constituents:

$$\partial v/\partial P|_s = X(\partial v_1/\partial P|_s) + (1-X)(\partial v_2/\partial P|_s) \quad (7)$$

Or $$(-gv^2)/c^2 = X(-gv_1^2)/c_1^2 + (1-X)(-gv_2^2)/c_2^2 \quad (8)$$

Canceling the (−g) term from both sides of equation (8):

$$v^2/c^2 = X(v_1^2/c_1^2) + (1-X)(v_2^2/c_2^2) \quad (9)$$

It is noted that equation (9) is the square of the acoustic admittance of the mixture—the admittance characterizing the velocity/pressure quotient of the two mixture components in parallel.

Figure 1:
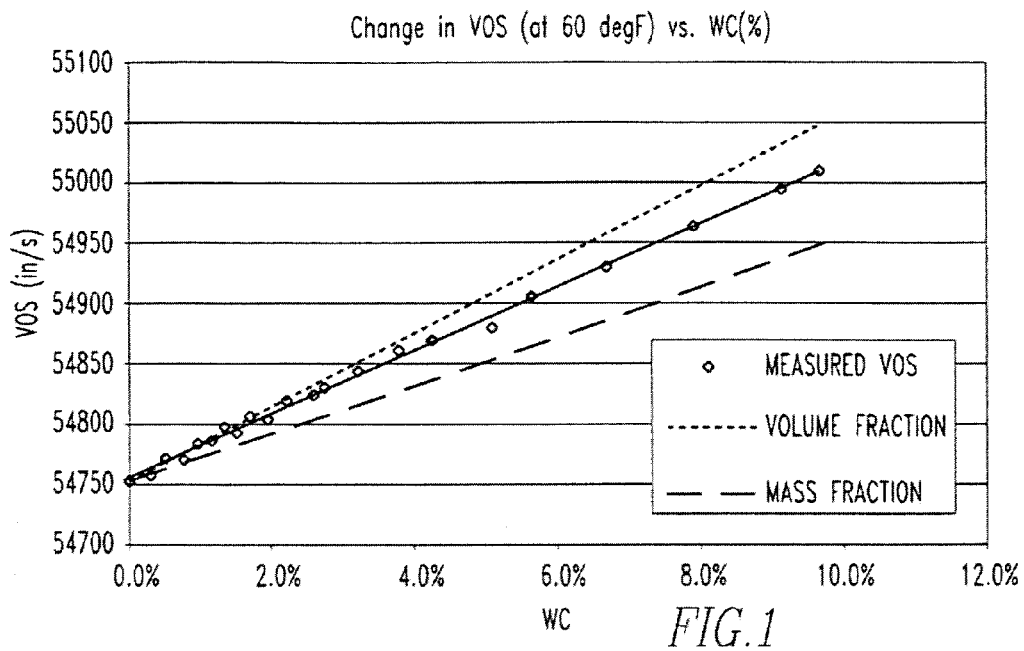
FIG. 1 shows change in VOS (at 60 degF) vs. WC(%).

FIG. 1 plots the sound velocity measured for a mixture of water and oil, each having known properties, against the mass fraction of water in the mixture, for a limited range of water mass fractions (0 to 10%). It should be noted that this document uses the term "water cut" as a synonym for the mass fraction of water, X, as defined above. Strictly speaking water cut is the volume fraction of water. The relationship between the two terms is straightforward, if the specific gravities of the constituents are known. The volume fraction of water in the mixture $V_1/(V_1+V_2)$ is given by $M_1v_1/(M_1v_1+M_2v_2)$ where $v_1$ and $v_2$ are the specific volumes of the water and oil respectively. This expression can be converted to the following form:

$$V_1/(V_1+V_2) = Xv_1/(Xv_1+(1-X)v_2).$$

FIG. 1 also plots the mixture sound velocity calculated using equation (1) against the water mass fraction. The calculated mixture sound velocity (the "mass weighted" velocity of the figure) is lower than the measured velocity by about 0.1%. [A volume weighted calculated velocity, on the other hand, is about 0.07% higher than the measured sound velocity. The volume weighted figure is of doubtful physical significance.] The source of the discrepancy between sound velocity predicted by equation (1) and the measured sound velocity may be due to the configuration of the experiment but may also be due to slip—the velocity of the dispersed phase, water in this case, is not necessarily the same as that of the continuous phase. Equation (1) takes no account of slip. Furthermore, slip can vary with the specifics of the measurement. To achieve full emulsification a fluid velocity of 10 feet/second or more is required; at this velocity droplets are very small. At velocities above 10 feet/second, the drag forces on a droplet, which pull it along with a velocity approaching that of the continuous phase, overwhelm the gravitational forces on the droplet, leading to little or no slip. The velocity was in the 3 to 4 feet/second range. At this velocity, the drag forces on the larger droplets of the dispersed phase do not overwhelm gravitational forces and the water droplets will tend to travel at a lower velocity than the continuous oil phase.

Reiterating, slip can be avoided and emulsification assured if the mixture sound velocity is measured where the direction of flow is horizontal, and the fluid velocity is in excess of 10 feet/second. Any measurement using sound velocity as a determinant for water cut must adhere to this requirement.

A re-examination of equation (9) reveals several drawbacks to the use of mixture sound velocity alone to measure water cut. More specifically, the sound velocities of the constituent phases must be known precisely, for the conditions of the measurement, specifically the temperature of both phases and the salinity of the water phase. This becomes evident from the scale of FIG. 1—an oil temperature change of 3° F. can change the mixture sound velocity by 250 in/sec, which corresponds to a 10% change in water cut. Thus if one is to make a determination of water cut to within, say, ±1%, he must measure temperature to better than ±0.3° F., on an absolute basis.

As noted in the background section above, an additional difficulty with the direct use of mixture sound velocity to measure water cut arises if the constituent sound velocities and densities are equal or nearly so. This can readily be seen in equation (1); changes in K will produce no change in mixture sound velocity when the two phases have the same specific gravity and sound velocity.

Figure 2:
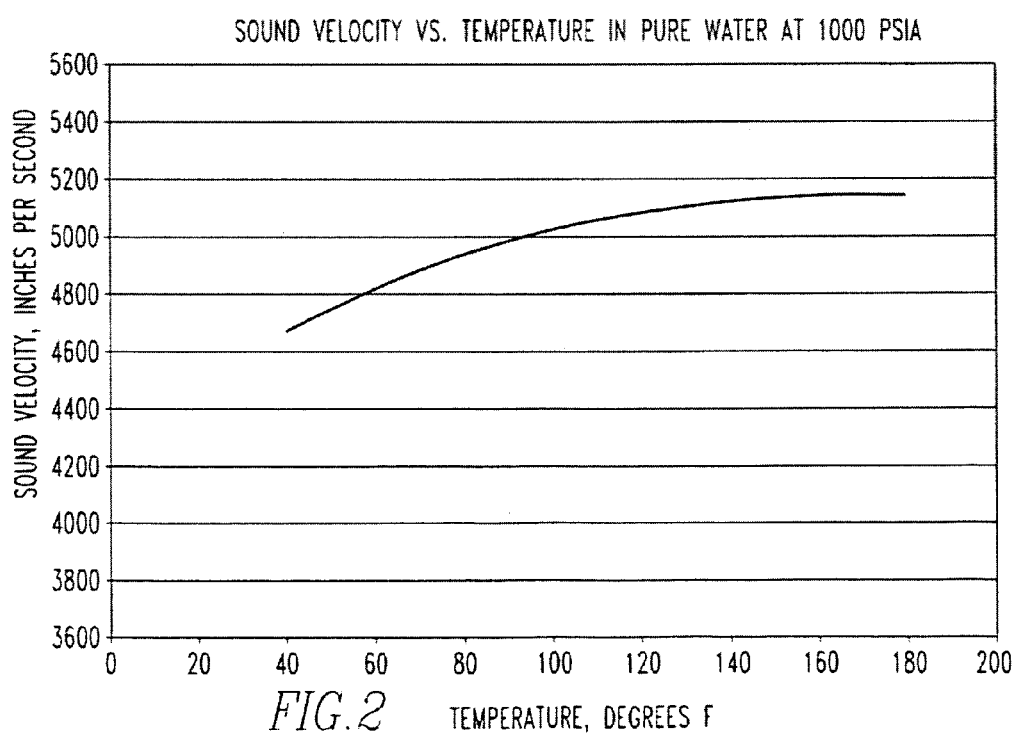
FIG. 2 shows sound velocity vs. temperature in pure water at 1000 psia.
Figure 3:
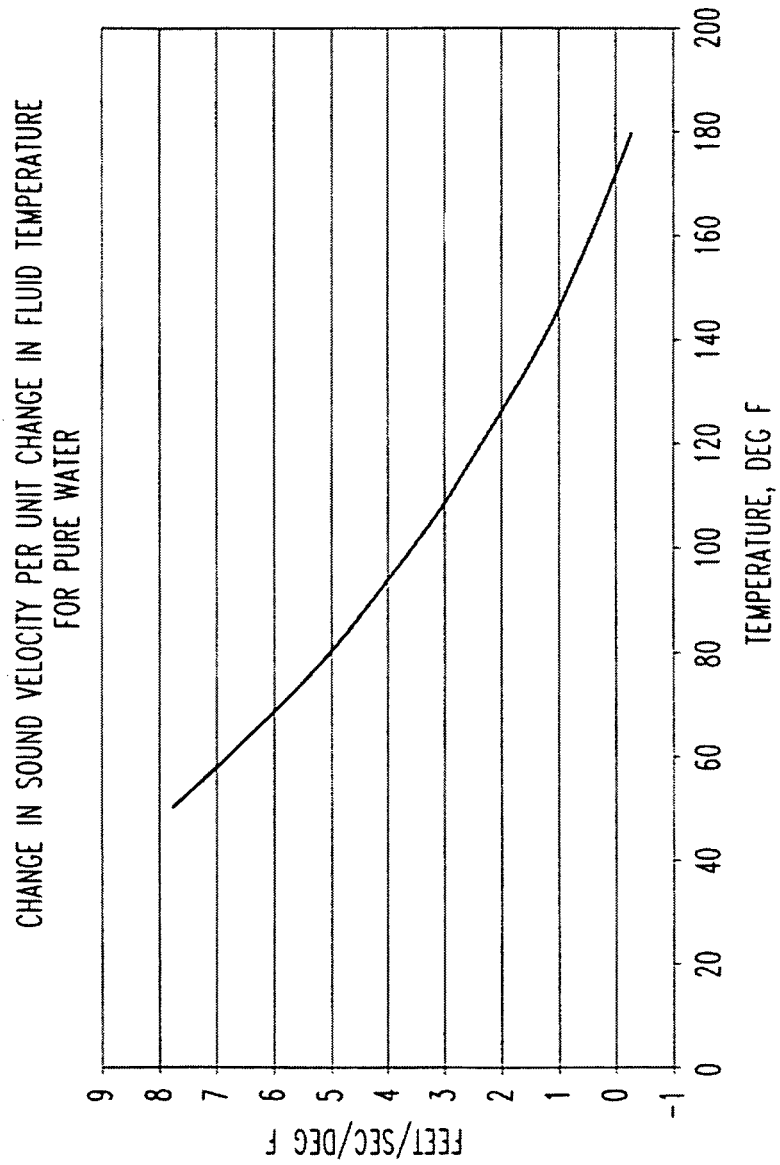
FIG. 3 shows change in sound velocity per unit change in fluid temperature for pure water.
Figure 4:
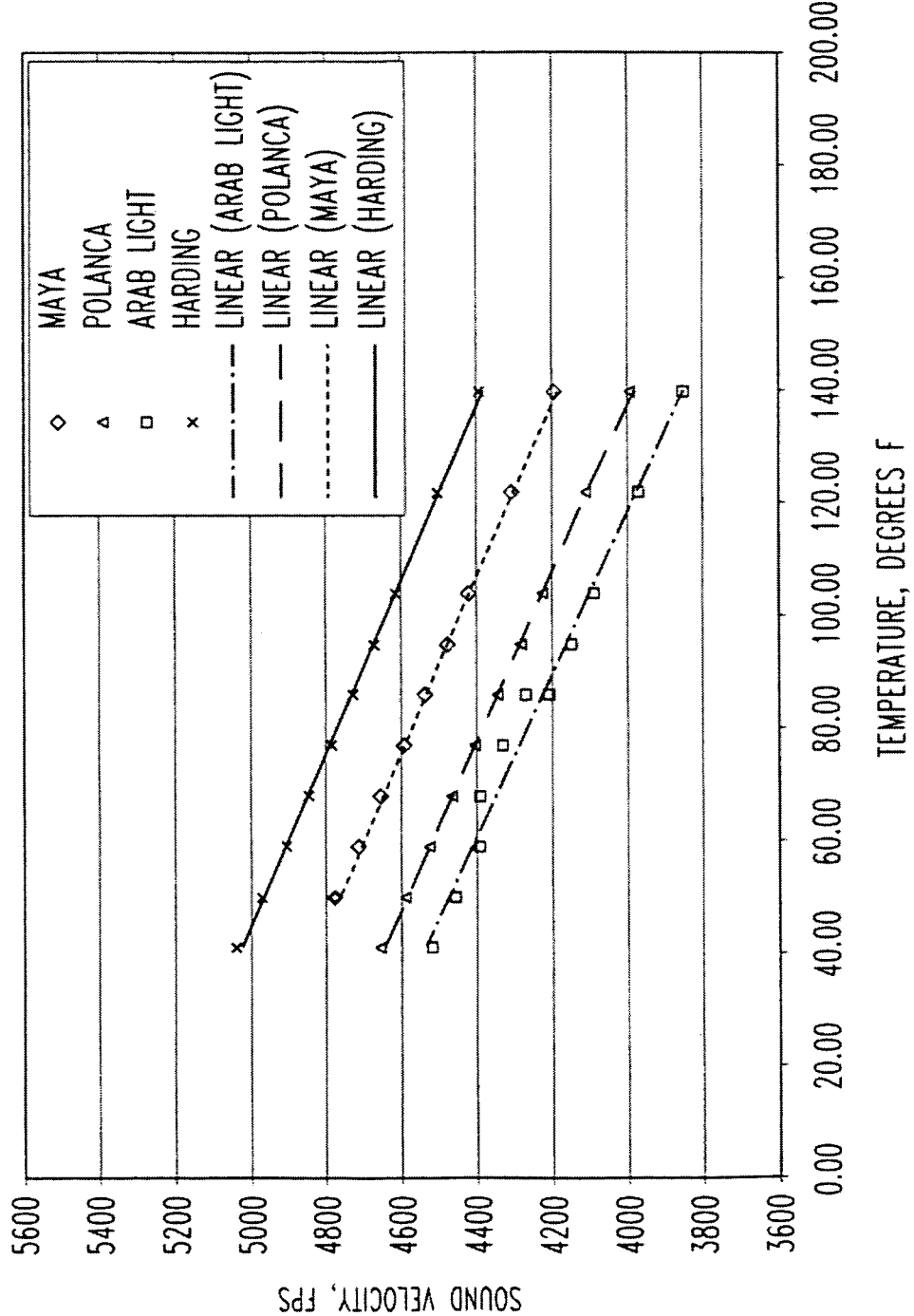
FIG. 4 shows sound velocity vs. temperature for several crude oils.
Figure 5:
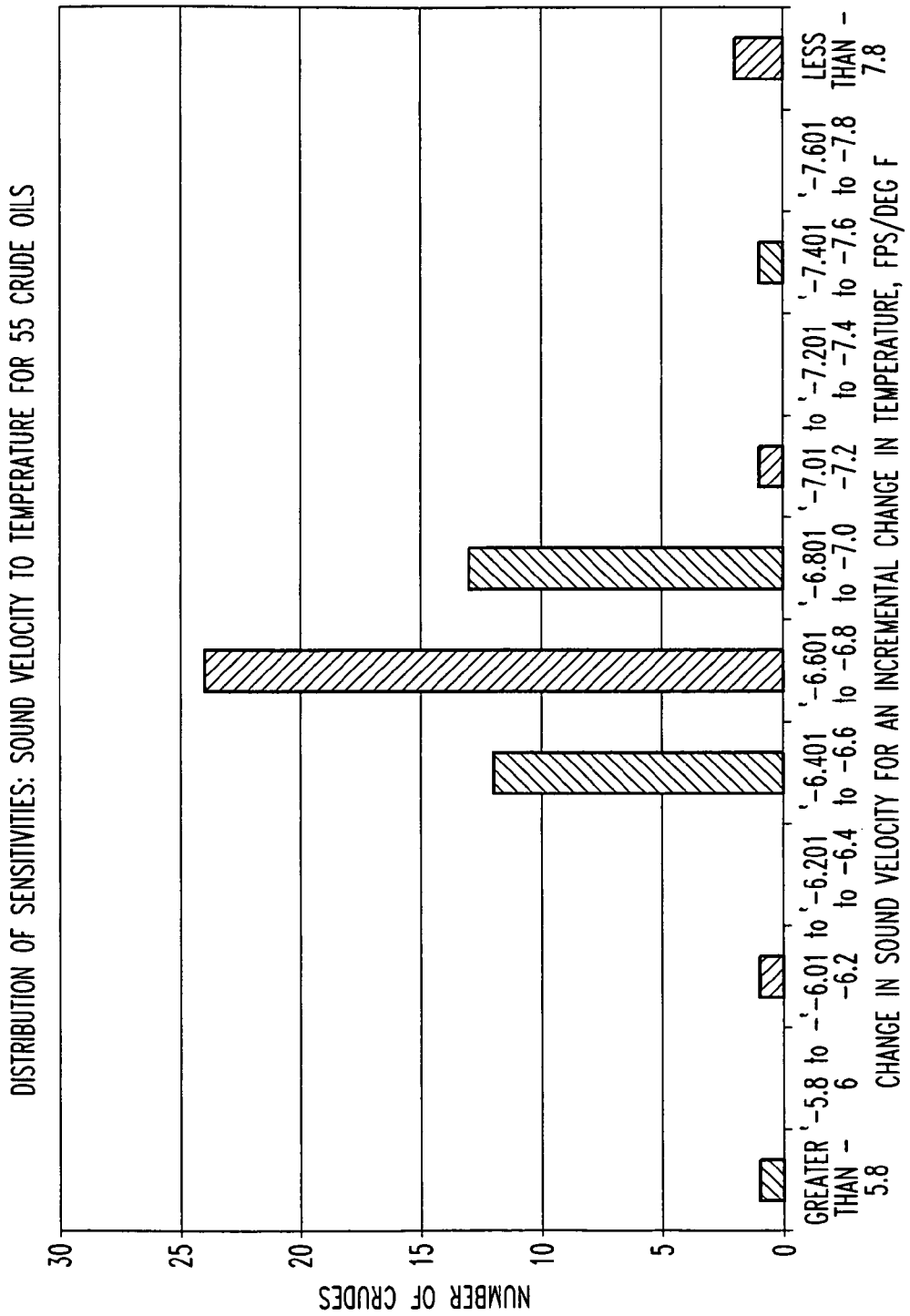
FIG. 5 shows distribution of sensitivities: sound velocity to temperature for 55 crude oils.

The means for measurement of water cut proposed herein exploits the responses of the constituents of a water-oil mixture to a change in temperature. The response of the sound velocity of water to an increase in temperature is very different from the response of the sound velocity of oil. The difference is evident from the data of FIGS. 2, 3, 4 and 5. The data of the figures describe the behavior of sound velocity with temperature for the temperature range in which most water cut measurements are made: 40° F. to 140° F. FIG. 2 plots the sound velocity of water against temperature; FIG. 3 plots the incremental change in sound velocity of water per degree Fahrenheit. FIG. 4 plots the sound velocity of four typical crudes covering a range of specific gravities, again against temperature. FIG. 5 is a bar chart showing the incremental change in sound velocity per degree Fahrenheit for 55 different crudes, in the temperature range of interest.

The difference in the responses of constituent sound velocities to a change in temperature is evident from a comparison of FIGS. 3 and 5. In water, an increase in temperature produces a change in sound velocity ranging from +7 fps/° F. at low temperatures to near zero at temperatures at the upper end of the range of interest. In most crude oils, an increase in temperature produces a change in sound velocity of about −6.7 fps/° F.±0.3 fps/° F., over the full temperature range. For all crudes the incremental change is negative, in contrast to that of water, which is either positive or zero, depending on its temperature.

Figure 6:
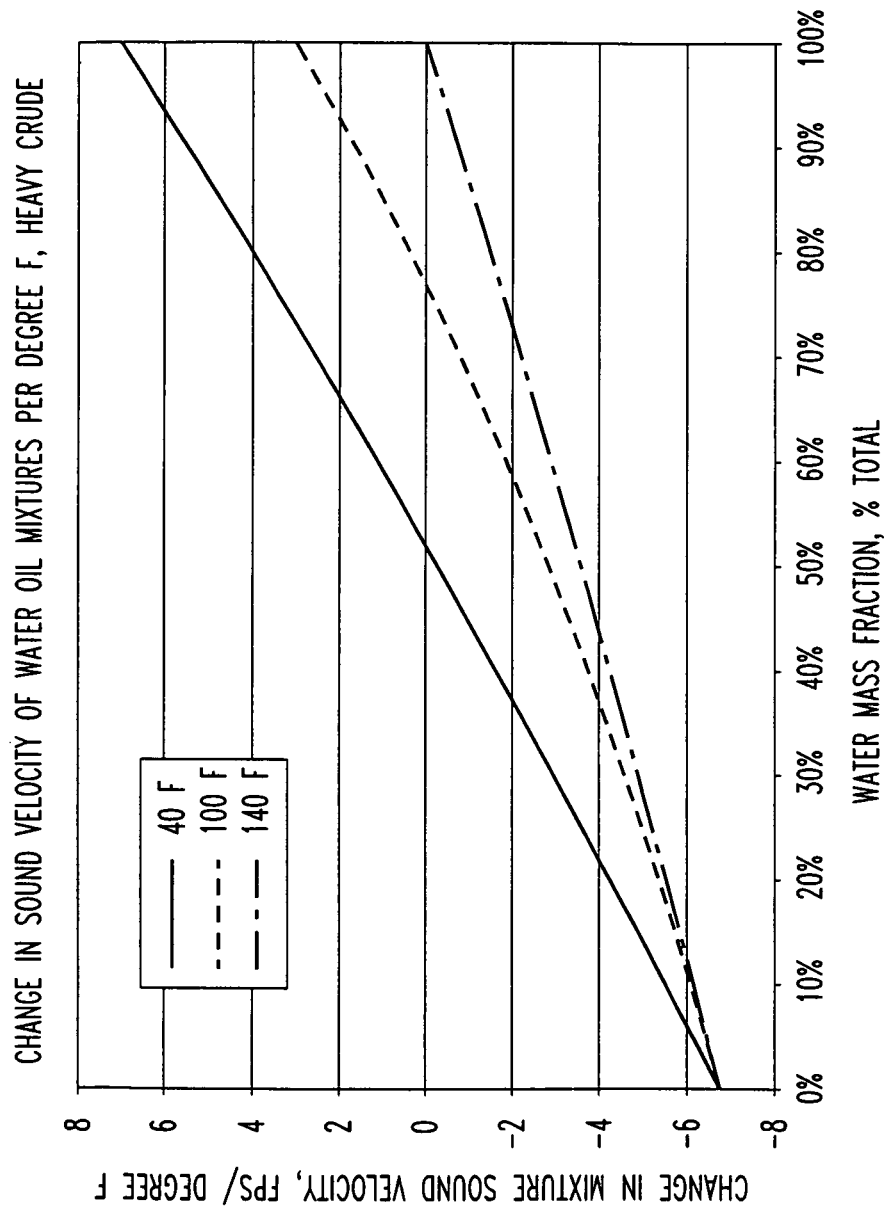
FIG. 6 shows change in sound velocity of water oil mixtures per degree F., heavy crude.
Figure 7:
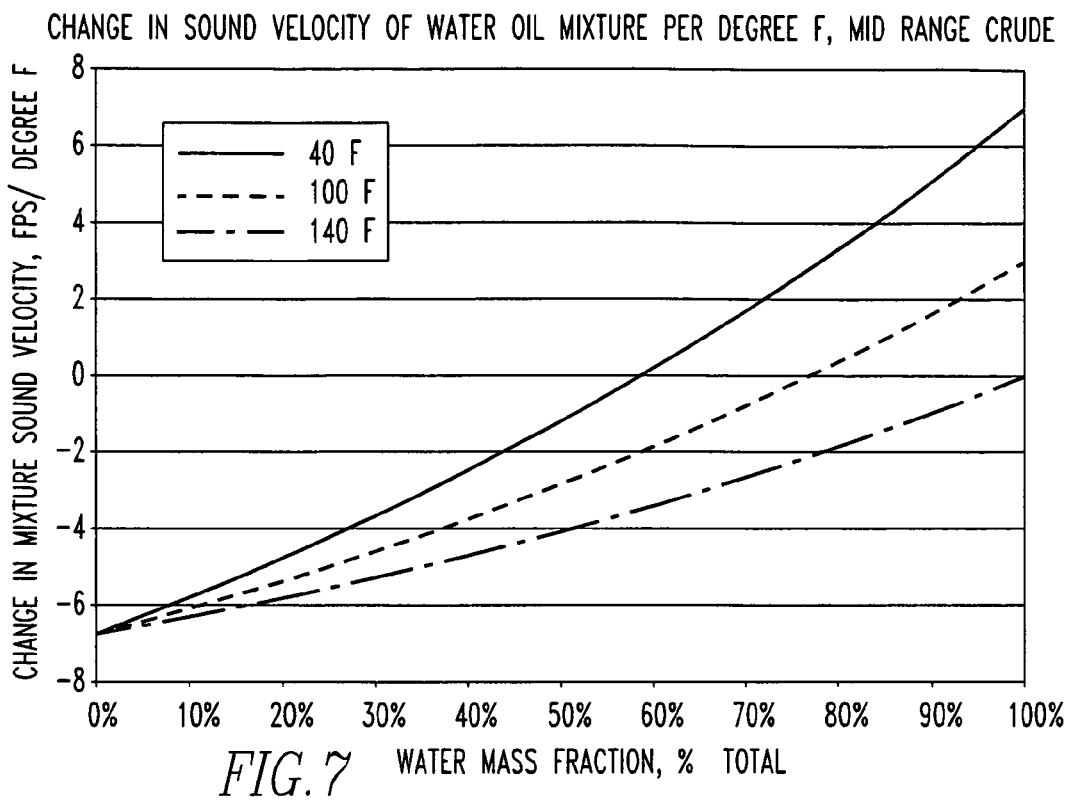
FIG. 7 shows change in sound velocity of water oil mixture per degree F., mid range crude.
Figure 8:
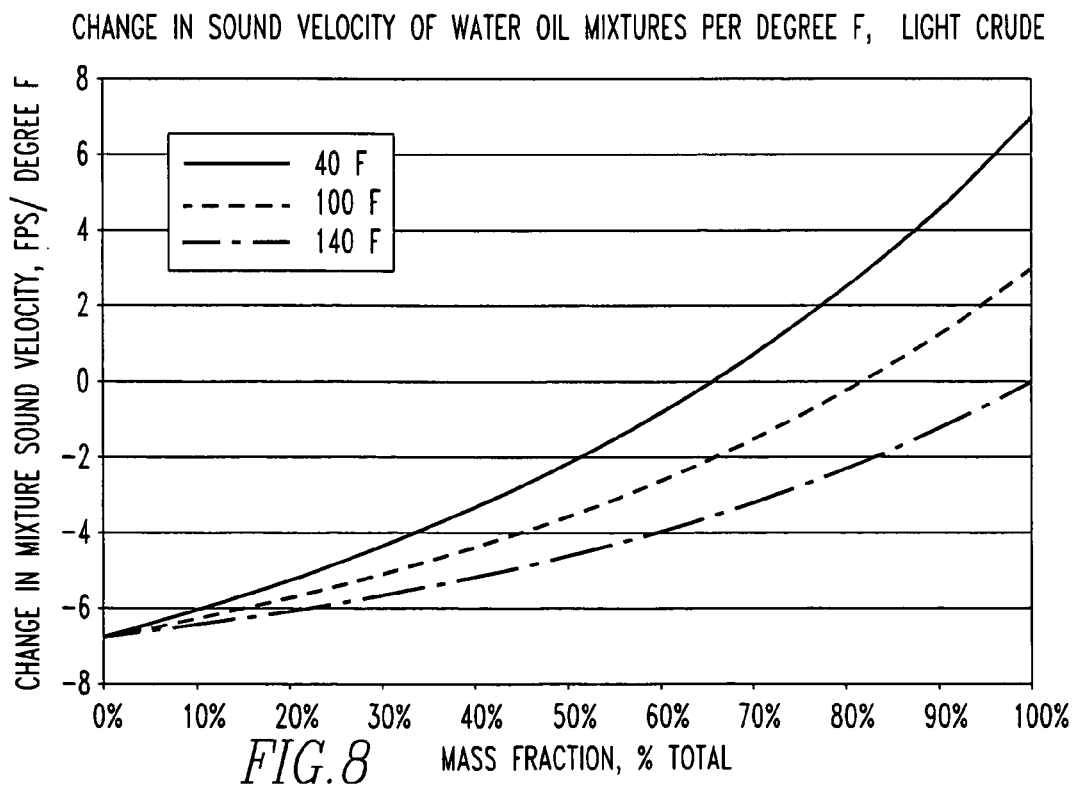
FIG. 8 shows change in sound velocity of water oil mixtures per degree F., light crude.

The principles of the proposed means for water cut measurement are illustrated in FIGS. 6, 7, and 8 which show the sound velocity changes for a 1° F. increase in mixture temperature over water mass fractions ranging from zero to 100%. FIG. 6 represents the response of a typical heavy crude, FIG. 7, a medium crude, and FIG. 8, a light crude. Each figure shows the sound velocity response for three different mixture temperatures covering the full range of potential applications: 40° F., 100° F., and 140° F. A comparison of the figures shows the strengths of a measurement using the proposed means for a mixture temperature change of only 1° F.:

- The left intercept (for 0% water cut) for all three figures is the same—−6.7 fps/° F. FIG. 5 shows that this figure is characteristic of many crudes, regardless of their specific gravity. FIG. 5 also shows that unlike water (FIG. 3), the slopes all the crude sound velocity-temperature curves are negative. Crude oil properties are well understood. The left intercept of the mixture sound velocity/temperature change vs. water cut curve can be firmly and accurately anchored for any crude.
- The right intercept (for 100% water cut) is likewise readily and precisely established using a temperature measurement of modest accuracy. The sound velocity versus temperature curve for pure water (FIG. 2) is extremely well documented in the scientific literature; the effect of salinity is likewise well documented and, with respect to the curve's slope, small. Accordingly, a measurement of the mixture temperature to within, say, ±2° F. allows the determination of the right intercept with precision, as illustrated by FIG. 3.
- The measurement does not depend heavily on knowledge of the sound velocities and specific gravities of the constituents. This follows from the shapes of the curves in FIGS. 6, 7, and 8. Between the two intercepts the curves do not depart greatly from a linear relationship (the curve for heavy crude at 40° F. is essentially linear). Scoping calculations, described in Appendix A, indicate that the proposed means can measure water cut with an accuracy of better than ±0.7% throughout the full range of water cuts (0% to 100%). This conclusion is subject to the following conditions:
  - Constituent sound velocities and gravities are established by a temperature measurement of ±2° F.,
  - A salinity estimate within a few thousand ppm is available,
  - The oil source is known and properties are established using existing oil property data bases.

Algorithm

The instrument utilizes measurements or estimates of the change in mixture properties with a measured change in temperature dT. Taking the derivative of equation (9) with respect to temperature:

$$d/dT(v^2/c^2) = X d/dT(v_1^2/c_1^2) + (1-X) d/dT(v_2^2/c_2^2) \quad 10)$$

$$2v/c^2 dv/dT - 2v^2/c^3 dc/dT = X(2v_1/c_1^2 dv_1/dT - 2v_1^2/c_1^3 dc_1/dT) + (1-X)(2v_2/c_2^2 dv_2/dT - 2v_2^2/c_2^3 dc_2/dT) \quad 11)$$

Here, again, the terms without subscripts refer to mixture properties, those with the subscript 1 refer to water properties, those with the subscript 2 refer to oil properties.

The term dv/dT on the left side of equation (11) can be expressed in terms of its constituents by taking the derivative of equation (1) with respect to temperature:

$$dv/dT = X dv_1/dT + (1-X) dv_2/dT \quad 12)$$

If the expression of equation (12) is substituted for dv/dT in equation 11 and the result solved for the mass fraction of water X, an expression of the following form is obtained:

$$X = B/A \quad 13)$$

Here:

$$B = dc/dT(v^2/c^3) - dc_2/dT(v_2^2/c_2^3) - dv_2/dT(v/c^2 - v_2/c_2^2) \quad 14)$$

$$A = dv_1/dT(v/c^2 - v_1/c_1^2) - dv_2/dT(v/c^2 - v_2/c_2^2) + dc_1/dT(v_1^2/c_1^3) - dc_2/dT(v_2^2/c_2^3) \quad 15)$$

All of the terms on the right hand sides of equations (14) and (15) are measured or can be estimated with reasonable accuracy from look-up tables. More specifically:

- $dc_2/dT$ is known for a wide range of crude oils. As noted in this disclosure it is usually close to 6.7 fps/° F.
- $dv_2/dT$ can be estimated from API or other tables relating crude oil density to temperature for a wide range of crudes and refined products. See, for example, the figure of page A-7 in Crane[1].

[1] Crane Technical Paper No. 410, incorporated by reference herein

- $v_2$ is estimated from those same lookup tables, based on a knowledge the specific volume for oil in the field from which the crude has been extracted and the temperature of the mixture as measured by an RTD at the inlet of the measurement apparatus.
- $c_2$ is estimated from those same tables, based on a knowledge the sound velocity for oil in the field from which the crude has been extracted and the temperature of the mixture measured by the RTD at the intake of the measurement apparatus.
- v is the specific volume of the mixture, as determined from the densitometer upstream of the inlet to the measurement apparatus. This variable can also be estimated from the mixture sound velocity and the properties of the constituents.
- c is the sound velocity of the mixture as measured by a single path ultrasonic transit time meter at the inlet of the measurement apparatus.
- dc/dT is determined from the measured difference in sound velocity between single path ultrasonic transit time meters at the inlet and exit of the measurement apparatus and the measured difference in temperature between RTDs at the inlet and exit of the measurement apparatus. Differential errors are minimized by "zeroing out" the sound velocity and temperature differences with no heating or cooling, using the 2 way valve, to bypass the cooler. This step is performed before commencing the measurements.

As noted previously, the petroleum industry generally characterizes the presence of water in a petroleum product as "water cut". Also as noted above, water cut is defined as the volume fraction of water present in an oil-water mixture. For a homogenous mixture without slip, volume fraction is related to the mass fraction X as determined by the algorithm of equations (13), 14) and (15) as follows:

$$VF = Xv_1/[Xv_1 + (1-X)v_2] \quad 16)$$

Implementation

FIGS. 9 and 10 illustrate one implementation of the present technique for water cut measurement. FIG. 9 shows an oil water mixture flowing in a pipe 12. The diameter of the pipe 12 is selected so as to maintain the mixture velocity above 10 feet per second, to ensure emulsification and minimal slip. The sample arrangement (4 taps 30 located at different radii within the pipe 12) enhances the precision of the measurement. Locating the taps 30 according to the rules of numerical integration (e.g., Gaussian quadrature) and weighting the mass fractions at each location as prescribed by the integration method allows the calculation of bulk average water cut with lower uncertainty.

The sample tap arrangement allows sampling to proceed from each tap in turn, through the operation of the solenoid valves S1 through S4. Each valve is maintained open for a period long enough to ensure representative sound velocity and temperature measurements for the associated tap location. The metering pump 26 ensures that the velocity of the mixture in the sample piping is maintained above that necessary to minimize slip and maintain emulsification.

FIG. 10 shows one arrangement of sensors for the measurement of sound velocity and temperature. The diameter of the sensor piping is chosen to ensure that, given the flow rate of the sample pump 26, the mixture remains emulsified. A sensor of the requisite accuracy—an RTD or thermocouple—measures the temperature of the incoming sample mixture. The sensor is located at the 90° inlet bend to ensure a measurement representative of the sample liquid. The sample is then directed through a second 90° bend in which is located a piezoceramic sound velocity transducer 34. The transducer is operated in the pulse echo mode. With appropriate signal processing, the sound velocity C of the mixture can be determined from the transit time t of a pulse of ultrasound that travels to the reflecting plug 36 of the sensor and back to the transducer:

$$C = 2L/t \quad 2)$$

Where L is the distance from the transducer face to the reflecting plug, and t is the round trip transit time in the fluid.

The diameter and frequency of the ultrasonic transducer and the configuration of the sensor tube are chosen to ensure that, given the diameter of the sensor assembly in the way of the transit time measurement, the walls of the sensor assembly due not interfere with the transit of the pulse. In addition this section of the sensor assembly is horizontal, to avoid gravitationally induced slip in the sample mixture. The effect of fluid velocity on the sound velocity measurement is intrinsically nullified by the pulse echo arrangement.

It should be noted that the pulse transit time measurements will include the travel times of the pulse through non fluid media—the delays of the cable, electronics, and the acoustic "window" of the transducer assembly. These delays can be calculated (or measured offline). In any event, a highly accurate determination of the delay in non fluid media is not required because the method relies entirely on the difference in sound velocities of the mixture at two different temperatures. Means for dealing with the difference in the delays of the two measurements in a manner consistent with the accuracy goals of the measurement are discussed further in Appendix A.

The electric heater downstream of the inlet sensor assembly in FIG. 9 raises the temperature of the mixture by a preset amount. As shown in Appendix A, the digitally based transit time measurement allows the determination of the difference in sound velocities, hot vs. cold, to within a few parts in 100,000, a temperature increase of as little as 2° F. is sufficient to produce an accurate measurement of the change in mixture sound velocity. Note that the proposed means can work just as effectively if the temperature of the sample is cooled by 2° F. The heater-cooler choice would be based on the temperature of the incoming oil-water mixture and the amount of power required to affect the heating versus the cooling.

Downstream of the heater (or cooler), the sample mixture is directed thorough the second sound velocity and temperature sensor assembly. After passing through this sensor assembly, the mixture is returned to the pipe 12 from which it was extracted.

To obtain the water cut, the algorithm described by equations (13), (14), (15), and (16) above is employed.

It should be pointed out that the data processing of the proposed system should account for the transport delay through the piping and the heater (or cooler) between the sensors which measure sound velocity and temperature at the upstream and downstream locations. The data processing must take the difference between the measurements at the hot (or cold) sensor and the measurements at the inlet sensor taken earlier by an amount equal to the transport delay. This measure is necessary because the water cut may vary in time; failure to account for the transport delay will introduce "noise" and possibly biases into the water cut measurement.

Heater power and flow rate affect the performance of the sample system illustrated in FIG. 9. Clearly, the system cost is minimized if power and flow rate requirements are low. On the other hand, accuracy is enhanced with increased temperature rise (or fall). And larger ultrasonic transducers can be accommodated in larger sensor pipe 12 diameters, which require higher flow. Larger transducers maximize the strength of the received ultrasonic signals while still avoiding interaction of the acoustic wave with the pipe 12 wall. Design tradeoffs are illustrated in the table below.

TABLE 1

Sample System Design Tradeoffs
Minimum Flow Velocity 10 fps, Sp. Gravity 1.0, Sp. Heat 1.0 btu/#/° F.

|  | System 1 | System 2 | System 3 |
|---|---|---|---|
| Temperature increase (or decrease) | 1° F. | 1° F. | 2° F. |
| Heater Power for increase | 2 kW | 5 kW | 5 kW |
| Flow Rate | 14 gpm | 34 gpm | 17 gpm |
| Sensor Pipe Diameter | 0.75 in. | 1.2 in | 0.83 in |

Appendix A analyzes the uncertainties in the measurement System 3 of the table above. It concludes that uncertainties in the measurement of water cut with this system are about ±½% water cut at water cuts near 0% and 100%. The uncertainties increase to about ±⅔% water cut in the mid range of water cuts (20% to 70%). Increasing the heating (or cooling) so as to double the temperature increase (or decrease) in system 3 would halve these uncertainties.

Implementation methods other than those illustrated in FIGS. 9 and 10 are possible. For example, in some pipelines a heater is employed at the head end, to increase oil temperature and thereby reduce pumping power requirements. Conventional temperature instruments upstream and downstream of the heater, along with conventional ultrasonic transducers (which can be mounted external to the upstream and downstream pipe) will provide inputs to a system that determines water cut using an algorithm similar to that described above. Again, data processing for such installations must account for the transport delay between the cold and hot sensor locations.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

APPENDIX A

Uncertainties for the Water Cut Calculation

Summary

This analysis establishes that systems of the type described herein, wherein the temperature of an emulsified oil-water mixture is increased or decreased 2° F., can measure water cut with an accuracy of better than ±0.67% water cut over the full range of water cuts. Accuracy approaches ±0.5% water cut at water cuts near 0% and 100%. These accuracies are calculated for System 3 herein. The accuracies can be halved, roughly, if heating (or cooling) is increased so as to double the temperature change.

Analysis

Design tradeoffs for systems to measure the water cut of a sample of a flowing water-oil mixture are given in a table herein. FIGS. 9 and 10 depict the arrangement of the sample measurement systems. In System 3 herein, a 5 kW heater provides a temperature rise of 2° F. for a sample flow rate of 17 gpm. This flow rate in a 0.83 inch diameter pipe 12 produces a fluid velocity of 10 feet/sec, which is assumed sufficient to ensure an emulsified sample with little slip. This system will be used as a reference to establish the accuracy of the measurements of the change in sound velocity and the change in temperature, as well as the accuracy of other fluid properties used to calculate the accuracy of the water cut determination over the full water cut range.

The accuracy objective for the water cut measurement—in the order of ±1% water cut—implies requirements on the accuracy of the measurements of the changes in mixture sound velocity $\Delta C$ and changes in mixture temperature $\Delta T$ produced by the heater of the reference system. An input mixture temperature in the 100° F. range was chosen for the analysis. For this mixture temperature, the mixture sound velocity change per unit temperature change, dC/dT, varies from −81 inches per second per °F. at 0% water, to +36 inches per second per °F. at 100% water cut. FIG. 12, produced from the analyses supporting the present invention, shows that, for a heavy crude, intermediate values of water cut are related to dC/dT by what is essentially a straight line connecting these end points. The medium and lighter crudes in this example share the same end points, but depart from linearity because of the differences in the properties of the constituents, specifically sound velocity and density (which is strongly correlated with sound velocity). A sensitivity analysis performed in support of the present invention demonstrated that, with an approximate knowledge of the constituent properties, a correction could be applied to the linear relationship to achieve good water cut accuracy (a quantitative analysis of this correction is given later in this analysis). But for all oils, the overall accuracy of the water cut determination rests on the accuracy of the dC/dT measurement: for this example, 1.17 inches per second per degree F. per % water cut. For the two degree F. change in the temperature of the sample of the reference system, this amounts to a 2.34 inch/sec change in sound velocity for a 1% change in water cut. So the issues are: (1) Can a change in mixture sound velocity of 2.34 inches per second be measured with sufficient accuracy to support a ±1% water cut measurement? and (2) Can a change in mixture temperature of 2° F. be measured with sufficient accuracy to support a ±1% water cut measurement?

Before addressing these issues, it should be noted that at product temperatures lower than the 100° F. assumed, the slope becomes higher; therefore the burden on the measurement accuracies of the change in sound velocity and the change in temperature is eased. On the other hand at higher product temperatures, 140° F., for example, the slope is lower. But in this case the designer has the option of cooling the sample by, say, 5 or 10° F., using the ambient as a heat sink. For these conditions, cooling requires the expenditure of very little power hence the burden on the measurements of the reduced slope can be economically offset by a much increased temperature change.

Algorithm for the Determination of $\Delta C$, the Change in Mixture Sound Velocity The sound velocity of crude oil-water mixtures is in the order of 55,000 inches per second, so that the requirement to detect and measure a change of 2.34 inches/second amounts to a precision requirement of about 1 part in 24,000. The sound velocity C as measured by the sensor assemblies of FIG. 10 is given as:

$$C = 2L/t \qquad \text{A-1)}$$

Here L is the distance in the fluid from the face of the transducer window to the reflecting plug, and t is the transit time in the fluid As stated above, the time that is measured will include not only the transit time in the fluid but the delays in the transmission of energy from a transmitter through cables, transducers, acoustic windows and signal detection electronics. Assuming for the moment that the non fluid delays, $\tau$, and path lengths for each sensor are equal, the sound velocities as measured by the sensors upstream (C) and downstream (H) of the heater element are, respectively:

$$C_C = 2L/(t_C - \tau) \qquad \text{A-2A}$$

$$C_H = 2L/(t_H - \tau) = 2L/(t_C + \Delta t - \tau) \qquad \text{A-2B}$$

Here $\Delta t$ is the difference in transit time produced by heating the fluid in the heater.

The difference in sound velocities, $\Delta C$ is given by $$\Delta C = C_H - C_C = 2L[1/(t_C + \Delta t - \tau) - 1/(t_C - \tau)] \qquad \text{A-3}$$

Multiplying both terms in the brackets by the product $(t_C + \Delta t - \tau)(t_C - \tau)$ the following expression is obtained for $\Delta C$:

$$\Delta C = 2L[(t_C - \tau) - (t_C + \Delta t - \tau)]/[(t_C + \Delta t - \tau)(t_C - \tau)] \qquad \text{A-4}$$

Carrying out the algebra in Equation (A-4):

$$\Delta C = -2L\Delta t/[(t_C + \Delta t - \tau)(t_C - \tau)] \cong -2L\Delta t/(t_C - \tau)^2 \qquad \text{A-4A}$$

The approximation of equation (A-4A) is justified as follows: For the sensors of the reference system, a path length L of 5 inches has been selected. With this path length, a ½ inch diameter, 3 MHz transducer produces a focused beam that does not interact with the 0.83 inch diameter tubular walls of the sensor. The net transit time in the fluid $(t_C - \tau)$ for a packet of 3 MHz acoustic energy with these parameters is nominally 167 μseconds at the inlet temperature of 100° F. The change in sound velocity produced by 2° F. of heating causes a change in transit time, $\Delta t$, of 6.5 nanoseconds for a change in water cut of 1%. Relative to $t_C$ the $\Delta t$ can therefore be neglected in the denominator product.

Uncertainty in the Determination of the Change in Mixture Sound Velocity

The uncertainty in the change in sound velocity $\partial \Delta C$ is found by taking the differential of equation A-4A. The result of this procedure is as follows:

$$\partial \Delta C = 2L/(t_C-\tau)^2 [-\partial \Delta t + 2\Delta t/(t_C-\tau)\partial(t_C-\tau) - \Delta t \partial L/L] \quad \text{A-5}$$

The uncertainties in path length $\Delta L$ and net transit time $\partial(t_C-\tau)$ are dominated by biases that do not vary with operating conditions. Their net impact can be determined by measuring the $\Delta t$ with the heater or cooler off (that is, with no temperature change between the two sensors). In this condition $\partial \Delta C = \Delta C = 0$. The measured residual $\Delta t$, $\partial \Delta t_0$, characterizes the net residual biases in transit time and path length, including those due to differences between the lengths and non fluid delays of the upstream and downstream sensors.

$$\partial \Delta t_0 = [2\Delta t/(t_C-\tau)\partial(t_C-\tau) - \Delta t \Delta L/L]_0 \quad \text{A-6}$$

Accordingly, the uncertainty in $\Delta C$ due to uncertainties in path length and non fluid delays can be minimized by algebraically combining $\partial \Delta t_0$ with the measured $\Delta t$ when the sample is being heated. It should be noted however that the correction $\partial \Delta t_0$ is subject to the same time measurement uncertainties as is the measurement of $\Delta t$, which uncertainties are described in the paragraphs that follow.

The residual uncertainty in $\Delta C$ is due to uncertainties in the time difference $\Delta t$ between the transit times measured by the hot and cold sound velocity sensors under operating conditions. Elements of the $\Delta t$ uncertainty are given in Table A-1 below.

TABLE A-1

Uncertainty Elements in Time Difference Measurements

| Time Difference Uncertainty Element | Value | Basis |
|---|---|---|
| Clock dt | $6.5 \times 10^{-4}$ ns | The same clock will be used for both hot and cold measurements. Long term wander tends to cancel in each t measurement. Clock accuracy is specified at ±0.01%. The figure given is 0.01% of the reference $\Delta t$. |
| Clock resolution | 0.016 ns | The uncertainty in a single measurement (0.625 ns) is reduced by multiple samples (60 seconds of sampling at a 50 Hz rate = 3000 samples). The uncertainties in each time measurement are combined as the root sum squares. |
| Random noise | 0.14 ns | A signal/random noise ratio of 10 was assumed. Uncertainty is reduced by multiple samples, as above. |
| Coherent noise | 1.88 ns | A conservative signal/coherent noise ratio of 40 was assumed. |
| $\Delta t$ error Reference System | 1.88 ns | Root sum squares of above elements, since they are not systematically correlated with one another |

These same uncertainties also apply to the measurement, with zero temperature change, of the net bias $\partial \Delta t_0$ due to differences in path length and non fluid delay. Thus the total uncertainty in the measurement of dC/dT, the change in sound velocity with temperature for the reference system is given by:

$$\partial \Delta C = 2L(t_C-\tau)^2 [(\partial \Delta t)^2 + (\partial \Delta t_0)^2]^{1/2} = C_C [(\partial \Delta t)^2 + (\partial \Delta t_0)^2]^{1/2}/(t_C-\tau) \quad \text{A-7}$$

Substituting numbers for the reference system:

$$\partial \Delta C = 55,000 \text{ in/s}[(1.88 \text{ ns})^2 + (1.88 \text{ ns})^2]^{1/2}/(167,000 \text{ ns}) = 0.88 \text{ inches/second} \quad \text{A-7A}$$

Relative to the change in mixture sound velocity $\Delta C$ brought about by the 2° F. temperature change of the reference system—2.34 inches/second/% water cut—the uncertainty in the sound velocity contributes an uncertainty in the measurement of a 1% change in water cut of 0.88/2.34=0.376 of 1%. Thus the differential sound velocity measurement uncertainty degrades the ability to measure a 1% change in water cut by ±0.38%.

Uncertainty in the Determination of the Mixture Temperature Change, $\Delta T$; Aggregate Uncertainty in the Determination of dC/dT The ±0.38% figure does not account for the uncertainty in the measurement of temperature rise, $\Delta T$, which is also used to determine dC/dT. For effective measurement of water cut, the temperature measurement system must be designed to measure precisely the difference in the temperatures of the mixture upstream and downstream of the heat addition (or heat removal) device. FIG. 13 shows a sample schematic of a system for this purpose, using precision RTDs for both the hot leg and cold leg temperature measurements. Each RTD has a resistance of 100Ω at 32° F. with a sensitivity of approximately 0.214 Ω/° F. The 2° F. temperature rise of the reference system produces a differential voltage of 0.418 mv between each leg of the resistance bridge. For this analysis it has been assumed that this voltage can be measured within ±0.1 mv; thus the accuracy of the measurement of the temperature rise in the reference system is 0.1/0.418=0.24 for a 1% change in water cut or ±0.24% water cut.

As with the sound velocity differential, biases in the resistance bridge differential can be readily eliminated by measuring the differential voltage when no there is zero temperature difference between the "hot" and "cold" measurements (that is, no heating or cooling). Again, however, the differential voltage measurement with no heating or cooling is subject to its assumed uncertainty of ±0.1 mv. Accordingly the overall uncertainty of the temperature rise measurement is given by the root sum square of the uncertainty in the zero bias determination and the uncertainty in the determination with heating or $[2\times(0.24\%)^2]^{1/2}=\pm 0.34\%$.

The aggregate accuracy for the slope measurement dC/dT is the root sum square of the sound velocity and temperature components or $[(0.38\%)^2+(0.34\%)^2]^{1/2}=\pm 0.51\%$.

TABLE A-2

Uncertainties in the correction to a linear water cut vs. dC/dT curve

1. Uncertainty in correlation of sound velocity and temperature for saline water    ±36 inches per second TABLE A-2-continued Uncertainties in the correction to a linear water cut vs. dC/dT curve

| | |
|---|---|
| 2. Uncertainty in correlation of sound velocity and temperature for the crude oil of the application | ±160 inches per second |
| 3. Uncertainty in the measurement of $C_1$-$C_2$ due to a ±2° F. uncertainty in the measurement of $T_C$ | ±234 inches per second |
| 4. Aggregate uncertainty due to constituent sound velocities (root sum squares of 1, 2, and 3) | ±286 inches per second |
| 5. Maximum water cut change light vs. heavy oil for a fixed dC/dT, FIG. 14 | 14.9% |
| 6. Maximum sound velocity difference, light vs. heavy oil | 9600 inches per second |
| 7. Maximum uncertainty in water cut determination due to uncertainty in constituent sound velocities. [line 4/line 6] × line 5 | ±0.44% water cut |

Aggregate Uncertainty of the Water Cut Measurement

The ±0.44% uncertainty due to constituent properties is a maximum; as can be seen in FIG. 14 the corrections to a linear water cut vs. dC/dT relationship approach the 14.9% used in the table above only in the mid range of water cuts. In this range the total measurement uncertainty of the reference system is the root sum squares of the slope uncertainty, ±0.51% and the constituent uncertainty ±0.44% or ±0.67%. Thus, over the range of water cuts from 0% to 100% the uncertainty of the water cut measurement of the reference system lies between ±0.51% and 0.67% water cut depending on the water cut itself.

The invention claimed is:

1. An apparatus for measuring the mass fractions of water and oil in a flowing mixture of oil and water through a pipe comprising:
a sensor portion that measures sound velocity and temperature of the flowing oil water mixture at a first time and at a second time, the sensor portion includes a first sensor portion that measures the sound velocity and temperature of the flowing oil water mixture upstream of the temperature changer, and a second sensor portion that measures the sound velocity and temperature of the flowing mixture downstream of the temperature changer; and
a temperature changer in thermal communication with the flowing fluid which changes the temperature of the flowing oil water mixture by a measurable amount between the first time and the second time, the first sensor portion includes a sound velocity transducer and a reflecting plug, the sound velocity C of the mixture determined from the transit time t of a pulse of ultrasound from the transducer that travels to the reflecting plug of the sensor and back along axial flow with the flowing fluid to the transducer.

2. The apparatus as described in claim 1 wherein the temperature changer is either a heat exchanger that adds thermal energy to, or a cooler that removes thermal energy from the flowing mixture.

3. The apparatus as described in claim 2 including a controller and processor that determines the mass fraction of the water and oil through an algorithm stored on a non-transitory computer readable medium which is executed by the controller and processor that relates the mass fraction to the change in the sound velocity in the mixture for a known change in temperature.

4. The apparatus as described in claim 3 wherein the oil water mixture is emulsified so that droplets of a dispersed phase, which is either oil or water, are distributed throughout a continuous phase, which is either water or oil, said dispersal achieved by the flowing mixture moving at a velocity sufficient to achieve emulsification with no slip.

5. The apparatus as described in claim 4 including a pump in fluid communication with the mixture to ensure the velocity of the sample mixture is made to meet or exceed the emulsification velocity requirement and wherein a portion of the flowing oil water mixture is continuously sampled and passed through the first and second sensor portions and the temperature changer so as to allow determination of the change in mixture sound velocity for a measured change in temperature.

6. The apparatus as described in claim 4 including a pump in fluid communication with the mixture to ensure the velocity of the sample mixture is made to meet or exceed a emulsification velocity requirement and wherein several portions of the flowing oil water mixture are sampled, either continuously or successively, said samples, either singly or in combination pass through the first and second sensor portions and the temperature changer so as to allow the determination of the change in mixture sound velocity for a measured change in temperature for each sample location.

7. The apparatus as described in claim 5 including a sampling arrangement for sampling the fluid in communication with the first sensor portion.

8. The apparatus as described in claim 7 wherein the sampling arrangement includes a plurality of taps disposed at different radii in the pipe which sample the mixture.

9. The apparatus as described in claim 8 wherein the sampling arrangement includes valves for each tap that are maintained open for a period long enough to ensure a representative sound velocity and temperature measurement for the associated tap location.

10. An apparatus for measuring the volume fractions of water and oil in a flowing homogenous mixture of oil and water through a pipe comprising:
a sensor portion that measures sound velocity and temperature of the flowing oil water mixture at a first time and at a second time;
a temperature changer in thermal communication with the flowing fluid which changes the temperature of the flowing oil water mixture by a measurable amount between the first time and the second time; and
a controller and processor in communication with the sensor portion that determines the volume fraction VF of the flowing homogenous water and oil mixture without slip according to $$VF = Xv_1/[Xv_1 + (1-X)v_2], \text{ where}$$

X is a mass fraction of the oil and water mixture and X=B/A,
Here $$B = dc/dT(v^2/c^3) - dc_2/dT(v_2^2/c_2^3) - dv_2/dT(v/c^2 - v_2/c_2^2),$$

$$A = dv_1/dT(v/c^2 - v_1/c_1^2) - dv_2/dT(v/c^2 - v_2/c_2^2) + dc_1/dT(v_1^2/c_1^3) - dc_2/dT(v_2^2/c_2^3),$$

$v_1$ and $v_2$ are specific volumes of the water and oil respectively and subscripts 1 and 2 refer to water and oil respectively,
c is a sound velocity of the mixture, and
dT is change in temperature.

11. A method for measuring water mass fraction in a flowing mixture of oil and water through a pipe comprising the steps of:

measuring sound velocity and temperature of the flowing oil water mixture at a first time with a first sensor portion of a sensor portion upstream of a temperature changer;

determining the sound velocity C of the mixture from the transit time t of a pulse of ultrasound from a transducer that travels to a reflecting plug of the first sensor portion and back along axial flow with the flowing fluid to the transducer;

changing the temperature of the flowing oil water mixture by a measurable amount with the temperature changer in thermal communication with the flowing fluid; and measuring sound velocity and temperature of the flowing oil water mixture at a second time with a second sensor portion of the sensor portion downstream of the temperature changer.

12. The method as described in claim 11 wherein the temperature changer is either a heat exchanger that adds thermal energy to, or a cooler that removes thermal energy from the flowing mixture.

13. The method as described in claim 12 including the step of determining the mass fraction of the water through an algorithm stored on a non-transitory computer readable medium which is executed by a controller and processor that relates the mass fraction to the change in the sound velocity in the mixture for a known change in temperature.

14. The method as described in claim 13 including the step of emulsifying the oil water mixture so that droplets of a dispersed phase, which is either oil or water, are distributed throughout a continuous phase, which is either water or oil, said dispersal achieved by the flowing mixture moving at a velocity sufficient to achieve emulsification with no slip.

15. The method as described in claim 14 including the step of pumping the mixture with a pump in fluid communication with the mixture to ensure the velocity of the sample mixture is made to meet or exceed the emulsification velocity requirement and wherein a portion of the flowing oil water mixture is continuously sampled and passed through the first and second sensor portions and the temperature changer so as to allow determination of the change in mixture sound velocity for a measured change in temperature.

16. The method as described in claim 15 including the step of pumping the mixture with a pump in fluid communication with the mixture to ensure the velocity of the sample mixture is made to meet or exceed the emulsification velocity requirement and wherein several portions of the flowing oil water mixture are sampled, either continuously or successively, said samples, either singly or in combination pass through the first and second sensor portions and the temperature changer so as to allow the determination of the change in mixture sound velocity for a measured change in temperature for each sample location.

17. The method as described in claim 16 including the step of sampling the fluid with a sampling arrangement in communication with the first sensor portion.

18. The method as described in claim 17 wherein the sampling step includes the step of sampling the mixture with a plurality of taps disposed at different radii in the pipe of the sampling arrangement.

19. The method as described in claim 18 including maintaining open valves of each tap of the sampling arrangement for a period long enough to ensure a representative sound velocity and temperature measurement for the associated tap location.

20. An apparatus for measuring the mass fractions of water and oil in a flowing mixture of oil and water through a pipe comprising:

a sensor portion that measures sound velocity and temperature of the flowing oil water mixture at a first time and at a second time, the sensor portion includes a first sensor portion that measures the sound velocity and temperature of the flowing oil water mixture upstream of the temperature changer, and a second sensor portion that measures the sound velocity and temperature of the flowing mixture downstream of the temperature changer;

determining the sound velocity C of the mixture from the transit time t of a pulse of ultrasound from a transducer that travels to a reflecting plug of the first sensor portion and back along axial flow with the flowing fluid to the transducer;

a temperature changer in thermal communication with the flowing fluid which changes the temperature of the flowing oil water mixture by a measurable amount between the first time and the second time, the temperature changer is either a heat exchanger that adds thermal energy to, or a cooler that removes thermal energy from the flowing mixture, the oil water mixture is emulsified so that droplets of a dispersed phase, which is either oil or water, are distributed throughout a continuous phase, which is either water or oil, said dispersal achieved by the flowing mixture moving at a velocity sufficient to achieve emulsification with no slip;

a controller and processor that determines the mass fraction of the water and oil through an algorithm stored on a non-transitory computer readable medium which is executed by the controller and processor that relates the mass fraction to the change in the sound velocity in the mixture for a known change in temperature;

a pump in fluid communication with the mixture to ensure the velocity of the sample mixture is made to meet or exceed the emulsification velocity requirement and wherein a portion of the flowing oil water mixture is continuously sampled and passed through the first and second sensor portions and the temperature changer so as to allow determination of the change in mixture sound velocity for a measured change in temperature; and a sampling arrangement for sampling the fluid in communication with the first sensor portion, the sampling arrangement includes a plurality of taps disposed at different radii in the pipe which sample the mixture, the sampling arrangement includes valves for each tap that are maintained open for a period long enough to ensure a representative sound velocity and temperature measurement for the associated tap location.

21. A method for measuring water mass fraction in a flowing mixture of oil and water through a pipe comprising the steps of:

emulsifying the oil water mixture so that droplets of a dispersed phase, which is either oil or water, are distributed throughout a continuous phase, said dispersal achieved by the flowing mixture moving at a velocity sufficient to achieve emulsification with no slip by pumping the mixture with a pump in fluid communication with the mixture to ensure the velocity of the sample mixture is made to meet or exceed the emulsification velocity requirement and wherein a portion of the flowing oil water mixture is continuously sampled and passed through the first and second sensor portions and the temperature changer so as to allow determination of the change in mixture sound velocity for a measured change in temperature;

measuring sound velocity and temperature of the flowing oil water mixture at a first time with a first sensor portion of a sensor portion upstream of a temperature changer, the temperature changer is either a heat exchanger that adds thermal energy to, or a cooler that removes thermal energy from the flowing mixture;

determining the sound velocity C of the mixture from the transit time t of a pulse of ultrasound from a transducer that travels to a reflecting plug of the first sensor portion and back along axial flow with the flowing fluid to the transducer;

determining the mass fraction of the water through an algorithm stored on a non-transitory computer readable medium which is executed by a controller and processor that relates the mass fraction to the change in the sound velocity in the mixture for a known change in temperature;

sampling step includes the step of sampling the mixture with a plurality of taps disposed at different radii in the pipe of the sampling arrangement;

maintaining open valves of each tap of the sampling arrangement for a period long enough to ensure a representative sound velocity and temperature measurement for the associated tap location;

changing the temperature of the flowing oil water mixture by a measurable amount with the temperature changer in thermal communication with the flowing fluid; and measuring sound velocity and temperature of the flowing oil water mixture at a second time with a second sensor portion of the sensor portion downstream of the temperature changer.

* * * * *